(12) United States Patent
De Wijs et al.

(10) Patent No.: US 11,357,472 B2
(45) Date of Patent: Jun. 14, 2022

(54) ROTATION DETERMINATION IN AN ULTRASOUND BEAM

(71) Applicant: KONINKLIJKE PHILIPS N.V., Eindhoven (NL)

(72) Inventors: Willem-Jan Arend De Wijs, Oss (NL); Alexander Franciscus Kolen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 522 days.

(21) Appl. No.: 16/061,287

(22) PCT Filed: Dec. 1, 2016

(86) PCT No.: PCT/EP2016/079356
§ 371 (c)(1),
(2) Date: Jun. 11, 2018

(87) PCT Pub. No.: WO2017/102338
PCT Pub. Date: Jun. 22, 2017

(65) Prior Publication Data
US 2018/0360413 A1 Dec. 20, 2018

(30) Foreign Application Priority Data
Dec. 15, 2015 (EP) .................................... 15200090

(51) Int. Cl.
*A61B 8/08* (2006.01)
*A61B 8/00* (2006.01)
(Continued)

(52) U.S. Cl.
CPC .............. *A61B 8/0841* (2013.01); *A61B 8/12* (2013.01); *A61B 8/145* (2013.01); *A61B 8/4488* (2013.01);
(Continued)

(58) Field of Classification Search
CPC ......... A61B 8/0841; A61B 8/12; A61B 8/145; A61B 8/4488; A61B 8/5246; A61B 8/15;
(Continued)

(56) References Cited

U.S. PATENT DOCUMENTS

| 5,636,255 A | 6/1997 | Ellis |
| 5,830,144 A | 11/1998 | Vesely |
| 6,216,029 B1 | 4/2001 | Paltieli |
| 2004/0193042 A1* | 9/2004 | Scampini ............... A61B 8/483 600/424 |

(Continued)

FOREIGN PATENT DOCUMENTS

| JP | 11076241 A | 3/1999 |
| WO | 199822179 A2 | 5/1998 |
| WO | 2011138698 A1 | 11/2011 |

*Primary Examiner* — Amelie R Davis
*Assistant Examiner* — John Denny Li

(57) ABSTRACT

The present invention relates to determining the rotation of an interventional device in an ultrasound field. An interventional device is provided that is suitable for being tracked in an ultrasound beam of a beamforming ultrasound imaging system by correlating transmitted ultrasound signals from the beamforming ultrasound imaging system as detected by ultrasound receivers attached to the interventional device with the beamforming beam sequence of the ultrasound signals. The interventional device includes a longitudinal axis (A-A'), a first linear sensor array (12) comprising a plurality of ultrasound receivers ($R_{1 \ldots n}$) wherein each ultrasound receiver has a length (L) and a width (W), and wherein the array extends along the width (W) direction. Moreover the first linear sensor array (12) is wrapped circumferentially around the interventional device with respect to the axis (A-A') such that the length (L) of each ultrasound receiver is arranged lengthwise with respect to the axis (A-A').

19 Claims, 4 Drawing Sheets

(51) Int. Cl.
*A61B 8/12* (2006.01)
*A61B 34/20* (2016.01)
*A61B 8/14* (2006.01)
*A61B 17/34* (2006.01)
*A61B 8/15* (2006.01)
*A61M 25/01* (2006.01)

(52) U.S. Cl.
CPC ........ *A61B 8/5246* (2013.01); *A61B 17/3403* (2013.01); *A61B 34/20* (2016.02); *A61B 8/15* (2013.01); *A61B 8/4245* (2013.01); *A61B 8/445* (2013.01); *A61B 8/4477* (2013.01); *A61B 8/4494* (2013.01); *A61B 8/5207* (2013.01); *A61B 2017/3413* (2013.01); *A61B 2034/2063* (2016.02); *A61B 2034/2065* (2016.02); *A61M 2025/0166* (2013.01)

(58) Field of Classification Search
CPC ..... A61B 8/4245; A61B 8/445; A61B 8/4477; A61B 8/4494; A61B 8/5207; A61B 34/20; A61B 17/3403; A61B 2034/2063; A61B 2034/2065; A61B 2017/3413; A61M 2025/0166
See application file for complete search history.

(56) References Cited

U.S. PATENT DOCUMENTS

| | | | |
|---|---|---|---|
| 2005/0261571 A1* | 11/2005 | Willis | A61B 8/0833 600/411 |
| 2006/0074319 A1* | 4/2006 | Barnes | A61B 5/06 600/466 |
| 2006/0079759 A1* | 4/2006 | Vaillant | A61B 34/20 600/424 |
| 2013/0310679 A1 | 11/2013 | Natarajan | |
| 2014/0276003 A1 | 9/2014 | Wang | |
| 2016/0100768 A1* | 4/2016 | Someya | A61B 5/0478 600/393 |
| 2016/0106391 A1* | 4/2016 | Jensen | G01S 15/8929 600/447 |
| 2016/0374710 A1* | 12/2016 | Sinelnikov | A61B 8/481 600/439 |

* cited by examiner

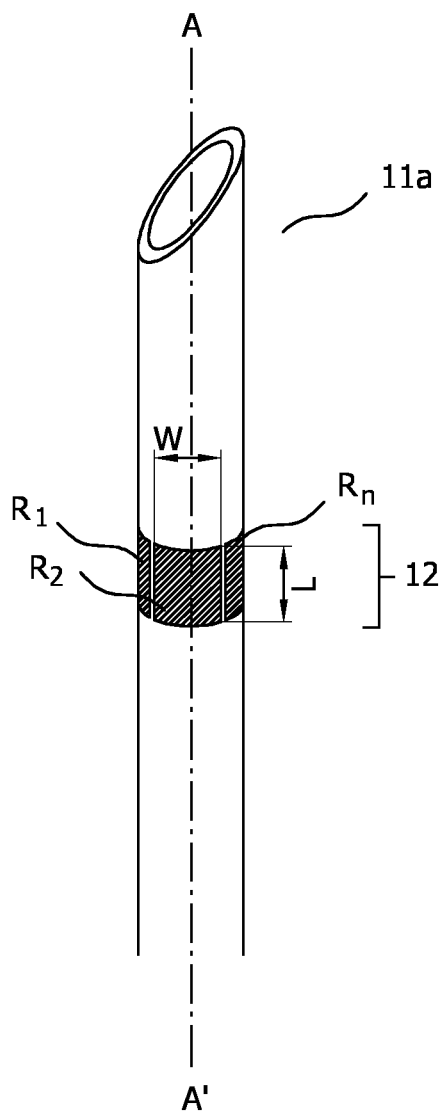
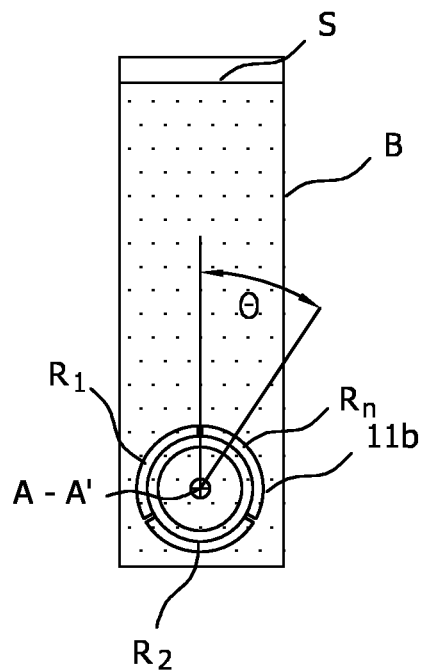
FIG. 1A
FIG. 1B
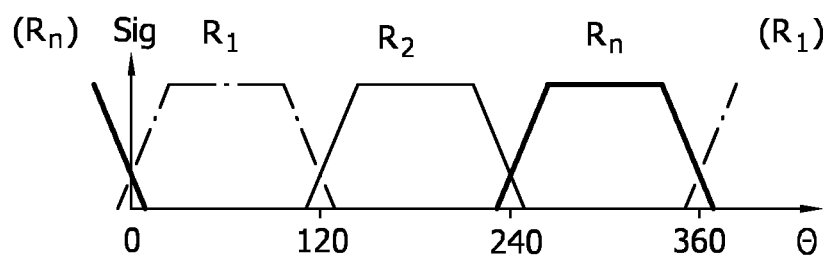
FIG. 1C

ROTATION DETERMINATION IN AN ULTRASOUND BEAM

CROSS-REFERENCE TO PRIOR APPLICATIONS

This application is the U.S. National Phase application under 35 U.S.C. § 371 of International Application No. PCT/EP2016/079356, filed on Dec. 1, 2016, which claims the benefit of European Patent Application No. 15200090.7, filed on Dec. 15, 2015. These applications are hereby incorporated by reference herein.

FIELD OF THE INVENTION

The present invention relates to determining the rotation of an interventional device in an ultrasound beam. The ultrasound beam may be a beam of medical ultrasound imaging system.

BACKGROUND OF THE INVENTION

Medical devices such as needles, catheters and interventional tools are often difficult to visualize in an ultrasound image due to the specular nature of their reflectivity, particularly at unfavorable incidence angles.

In one solution to this problem, publication WO/2011/138698 discloses to attach an ultrasound receiver to a medical device. The ultrasound receiver detects ultrasound signals from the ultrasound field of an ultrasound imaging probe, and processes these signals with an ultrasound receive beamformer. The ultrasound receive beamformer is configured for one-way only beamforming of transmissive ultrasound from the ultrasound field, and is used to track the position of the ultrasound receiver and thus the medical device in relation to the ultrasound field.

In another solution to this problem, U.S. Pat. No. 6,216,029B1 describes an arrangement for directing a needle towards a target within an ultrasound image. In this, the position of an ultrasound probe is determined in relation to a remotely-located position sensing unit by attaching three infrared ultrasonic transponders to the ultrasound probe. The transponders generate coded ultrasound signals in response to infrared signals emitted by infrared ultrasonic transceivers that form part of the position sensing unit. The ultrasound signals received by the position sensing unit provide triangulation information for the controller to calculate the position of the ultrasound probe in three dimensional space. U.S. Pat. No. 6,216,029B1 further describes a similar arrangement for locating the position of the needle respective the position sensing unit. Subsequently the trajectory of the needle point is displayed in the ultrasound image based on the positions of the ultrasound probe and the needle relative to the position sensing unit.

A document US20040193042A1 discloses a 3D ultrasonic diagnostic imaging system which is operated to guide an interventional device. In one example, ultrasound pulses from an ultrasound imaging probe are received by a transducer on the interventional device to determine its position based on the time of flight of the pulses.

SUMMARY OF THE INVENTION

In seeking to alleviate the drawbacks of known localization systems, an interventional device is provided which may be tracked in an ultrasound beam of a beamforming ultrasound imaging system. The device can be tracked using ultrasound receivers that are wrapped around the interventional device and which are configured to detect transmitted ultrasound signals from the ultrasound imaging system. The signals may be one-way transmitted ultrasound signals. The position of the ultrasound receivers and thus the position of the interventional device respective the beamforming ultrasound imaging system can be determined by correlating the transmitted ultrasound signals as detected by the ultrasound receivers with the beamforming beam sequence of the transmitted ultrasound signals. The interventional device includes a first linear sensor array of ultrasound receivers that are wrapped circumferentially around a longitudinal axis of the interventional device. Each ultrasound receiver has a length and a width, and the array extends along the width direction. The first linear sensor array is wrapped circumferentially around the interventional device with respect to the longitudinal axis such that the length of each ultrasound receiver is arranged lengthwise with respect to the axis. In so doing, an interventional device is provided in which the ultrasound receivers in the array have different viewing angles in a radial direction with respect to the longitudinal axis.

When the interventional device is located in a beam of a beamforming ultrasound imaging system the signals detected by each of the ultrasound receivers vary in accordance with the rotational angle of the interventional device about its longitudinal axis respective the origin of the beam. For example, an ultrasound receiver that is rotated relatively towards the origin of the ultrasound beam such that it faces the ultrasound beam will detect a relatively larger signal because it intercepts a relatively large cross sectional area of the beam. By contrast an ultrasound receiver that is rotated relatively away from the origin of the same ultrasound beam will detect a relatively smaller signal due to the relatively smaller cross-sectional beam area intercepted by the receiver. When the interventional device is rotated such that the ultrasound receiver is on the opposite side to the origin of the ultrasound beam the signal is further diminished owing to shadowing by the body of the interventional device.

Thus by comparing the relative magnitudes of the ultrasound signals detected by each ultrasound receiver on the interventional device, the rotation of the interventional device about its longitudinal axis can be determined in relation to the origin of the ultrasound beam. In a preferred operational mode the receiver, or group of receivers, that provide the maximum detected signal are thus used to identify the portion of the interventional device that is closest to the origin, i.e. the zenith, of the ultrasound beam. Alternatively the receiver, or group of receivers, that provide the earliest detected signal may be used to identify the portion of the interventional device that is closest to the origin, i.e. the zenith, of the ultrasound beam.

In accordance with another aspect of the invention the length of each ultrasound receiver in the first linear sensor array is greater that its width. This improves the axial range of the interventional device over which sensing can be achieved, and also improves the signal to noise ratio of signals detected by each receiver.

In accordance with another aspect of the invention, gaps between the ultrasound receivers are defined in relation to the ultrasound receiver width. This arrangement reduces the total rotational angle over which the interventional device has a reduced-sensitivity to ultrasound signals, thereby improving the accuracy with which the angular rotation can be determined.

In accordance with another aspect of the invention the first linear sensor array is wrapped around the longitudinal axis of the interventional device in the form of a spiral. The spiral wrapping arrangement provides a robust method of attaching the ultrasound transducers and the electrical interconnections associated therewith to interventional device. Moreover it provides an efficient arrangement for routing the electrical interconnections to the proximal end of the interventional device.

In accordance with another aspect of the invention the interventional device includes a second linear sensor array that is also wrapped around the interventional device circumferentially with respect to the longitudinal axis. Moreover, each gap between the ultrasound receivers in the first linear sensor array coincides with, or is aligned with, a receiver in the second linear sensor array in a lengthwise direction with respect to the axis. This arrangement improves the rotational sensitivity at rotational angles that correspond to the gaps of the first linear sensor array.

In accordance with another aspect of the invention the first linear sensor array comprises an even number of ultrasound receivers that are arranged in diametrically-opposing pairs with respect to the longitudinal axis. The ultrasound receivers are electrically connected such that ultrasound signals detected by the receivers in each pair are subtracted. This arrangement simplifies the complexity of the electrical interconnections associated with the ultrasound receivers.

Other aspects of the invention are defined in the independent claims, including various methods, a computer program product and an ultrasound imaging arrangement.

BRIEF DESCRIPTION OF THE FIGURES

FIG. 1 illustrates in FIG. 1A a side-view of an interventional device 11a that includes a first linear sensor array 12 of ultrasound receivers $R_{1 \ldots n}$ in accordance with a first aspect of the invention, and in FIG. 1B the same interventional device 11b in plan-view, positioned in an ultrasound beam B at rotational angle Θ to the origin of the beam at source S, and in FIG. 1C the signal, Sig, detected by each ultrasound receiver $R_1$, $R_2$, $R_n$, as the rotational angle Θ of the interventional device is varied.

DETAILED DESCRIPTION OF THE INVENTION

Figure 2:
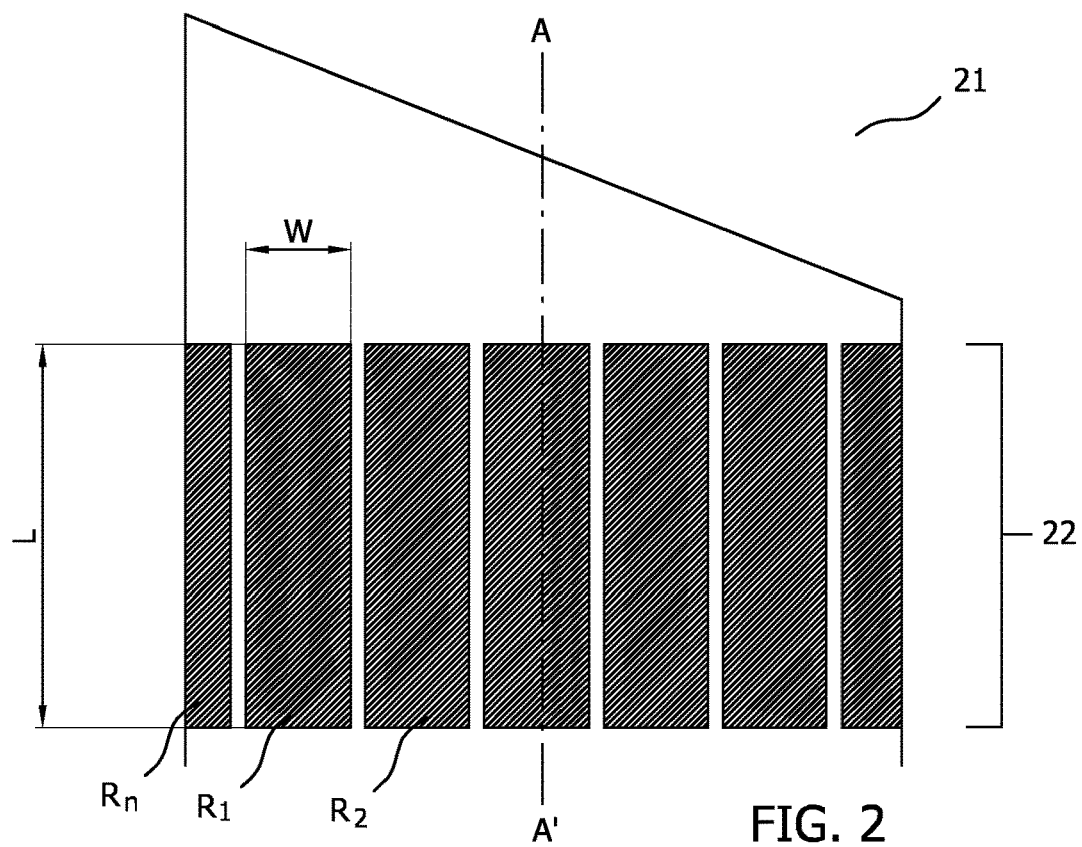
FIG. 2 illustrates in side-view a second embodiment of the invention in which the length L of each ultrasound receiver $R_1$, $R_2$, $R_n$ wrapped around longitudinal axis A-A' of interventional device 21 is greater than its width W.

In order to illustrate the principles of the present invention, various embodiments are described in which the interventional device whose rotation is determined is a needle. It is however to be appreciated that the invention also finds application in determining the rotation of other interventional devices such as a catheter, a guidewire, a probe, an endoscope, an electrode, a robot, a filter device, a balloon device, a stent, a mitral clip, a left atrial appendage closure device, an aortic valve, a pacemaker, an intravenous line, a drainage line, a surgical tool such as a tissue sealing device or a tissue cutting device. Moreover the embodiments described relate to determining the rotation of an interventional device in the various beams of a 2D ultrasound imaging probe as the beamforming ultrasound imaging system. It is also to be appreciated that the invention finds application with other types of beamforming ultrasound imaging systems such as a 3D imaging probe, a transesophageal probe (TEE), transthoracic probe (TTE), transnasal probe (TNE), intracardiac probe (ICE).

FIG. 1 illustrates in FIG. 1A a side-view of an interventional device 11a that includes a first linear sensor array 12 of ultrasound receivers $R_{1 \ldots n}$ in accordance with a first aspect of the invention, and in FIG. 1B the same interventional device 11b in plan-view, positioned in an ultrasound beam B at rotational angle Θ to the origin of the beam at source S, and in FIG. 1C the signal, Sig, detected by each ultrasound receiver $R_1$, $R_2$, $R_n$, as the rotational angle Θ of the interventional device is varied. The needle illustrated in FIG. 1A has a longitudinal axis A-A' about which linear sensor array 12 comprising three ultrasound receivers $R_1$, $R_2$, $R_n$ are wrapped circumferentially. Each ultrasound receiver has a length L and a width W and the array extends along the width direction. Thus, when the array is wrapped circumferentially around the interventional device with respect to the longitudinal axis A-A', the length L of each ultrasound receiver $R_1$, $R_2$, $R_n$ is arranged lengthwise with respect to the axis A-A'. In so doing, interventional device 11a is provided with three ultrasound receivers $R_1$, $R_2$, $R_n$ that have different radial viewing angles with respect to longitudinal axis A-A'. FIG. 1B illustrates the same interventional device as in FIG. 1A, i.e. item 11b in plan-view, positioned in an ultrasound beam B at rotational angle Θ to the origin of the beam at source S. Beam B may be an ultrasound beam of a beamforming ultrasound imaging system such as a 2D ultrasound imaging probe. The complete ultrasound field generated by the 2D ultrasound imaging probe typically comprises a fan of a plurality of beams such as beam B, which together are used to probe and thus generate a planar image of a slice through a region of interest. Thus at Θ=0° in FIG. 1B the beam origin at source S is between ultrasound receivers $R_1$ and $R_n$. As indicated, longitudinal axis A-A' of interventional device 11b is perpendicular the plane of the figure. With reference to FIG. 1B, FIG. 1C illustrates the signal, Sig, detected by each ultrasound receiver $R_1$, $R_2$, $R_n$, as the rotational angle Θ of the interventional device is varied. The angle Θ is the rotational angle about axis A-A' of the interventional device to the origin of the beam B. Thus as interventional device 11b is rotated clockwise from $\Theta=0°$ signal Sig initially increases towards its maximum for ultrasound receiver $R_1$, reaches a plateau, then decreases again towards $\Theta=120°$ at which angle the signal from ultrasound receiver $R_2$ starts to increase.

Since the ultrasound receivers $R_1$, $R_2$, $R_n$ in FIG. 1 are each sensitive to a portion of the complete 360° viewing angle around axis A-A', by comparing each of the signals detected by receivers $R_1$, $R_2$, $R_n$, the rotation $\Theta$ of the interventional device 11 about axis A-A' respective the origin of beam B can be determined. For example, when ultrasound receiver $R_1$ is rotated relatively towards ultrasound beam B such that it faces the center of source S of beam B, ultrasound receiver $R_1$ will detect a relatively larger signal because it intercepts the largest possible large cross sectional area of beam B. By contrast ultrasound receiver $R_2$ that at this rotational position is rotated relatively away from ultrasound beam B will detect a relatively smaller signal due to the reduced cross-sectional beam area intercepted by receiver $R_2$. When interventional device 11b is rotated such that ultrasound receiver $R_1$ is on the opposite side to the ultrasound beam, i.e. facing directly away from source S, its detected signal is further diminished owing to shadowing by the body of the interventional device 11b. This arrangement typically provides that each ultrasound receiver has maximum sensitivity in a substantially normal direction to axis A-A', i.e. within about ±10 degrees of the normal direction.

Thus by comparing the relative magnitudes of the ultrasound signals, $Sig_1$, $Sig_2$, $Sig_n$ detected by each ultrasound receiver $R_1$, $R_2$, $R_n$ the rotation of the interventional device 11b about its longitudinal axis A-A' can be determined in relation to the origin of ultrasound beam B, i.e. to the center of beam source S. In a preferred operational mode the ultrasound receiver, or group of receivers, that detect the maximum signal are used to indicate the portion of the interventional device that is closest to the center of source S, i.e. to the zenith, of ultrasound beam B. In an alternative operational mode the ultrasound receiver, or group of receivers, that detect the earliest signal are used to indicate the portion of the interventional device that is closest to the center of source S, i.e. to the zenith, of ultrasound beam B. These two modes can also be used in combination.

Whilst FIG. 1 illustrates a first linear sensing array 12 having three ultrasound receivers, two or more receivers are in principle sufficient for determining the rotation of the interventional device. This is because two receivers can be at least used to indicate which of the two possible 180° portions of the illustrated needle is closest to the center of source S. Clearly by increasing the number ultrasound receivers in the array the rotational angle sensed by each sensor decreases, thereby improving the angular resolution of the device. In arrangements which have a large number of receivers the signals from several ultrasound transducers may thus provide signals that are close to their maximum level. Thus it may be beneficial to determine the receiver that is closest to the center of ultrasound source S by analyzing the signals detected by the ultrasound receivers and determining the geometric center of the magnitudes of these detected signals, for example by fitting a function such as a Gaussian or a step-function to their spatial distribution and identifying the rotation based on the receiver that corresponds to the peak of the Gaussian function or to the center of the step function.

FIG. 2 illustrates in side-view a second embodiment of the invention in which the length L of each ultrasound receiver $R_1$, $R_2$, $R_n$ wrapped around longitudinal axis A-A' of interventional device 21 is greater than its width W. A drawback of improving the angular resolution of the linear sensing array of the FIG. 1 embodiment by reducing the width of each ultrasound receiver in the array is that this reduces the signal to noise ratio of signals detected by each ultrasound receiver. However the inventors have further realized that this reduction in signal to noise ratio can in part be compensated-for by increasing the length of each ultrasound receiver. Moreover, for the interventional devices contemplated by the present invention, increasing the length of each receiver in this way permits the determination of the rotation of the interventional device along a longer length of the axis A-A'. In so doing the rotation of the device can be determined when an otherwise shorter sensor would lie outside a finite ultrasound beam. This extension of the axis of the interventional device over which rotation can be determined is particularly useful in planar ultrasound imaging systems when an otherwise shorter sensor would lie in an out-of-plane position.

Figure 3:
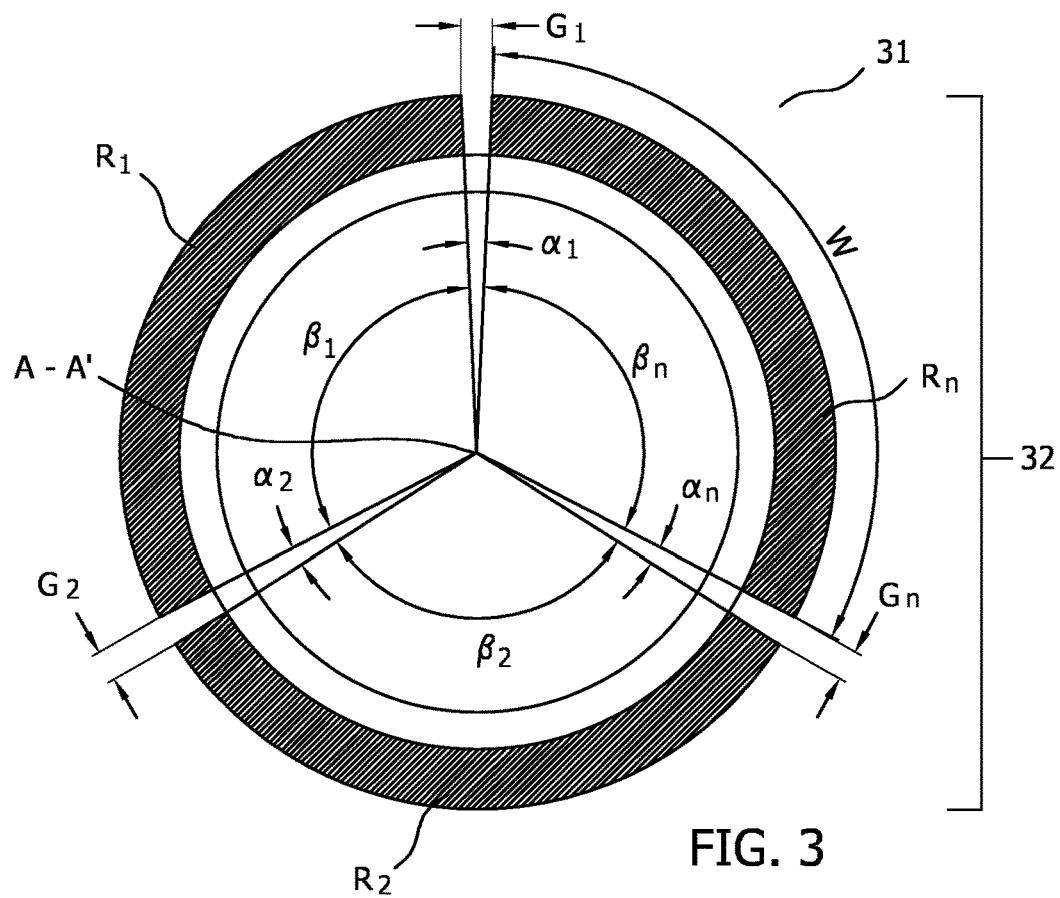
FIG. 3 illustrates in plan-view a third embodiment of the invention in which ultrasound receivers $R_1$, $R_2$, $R_n$ of first sensor array 32 that are wrapped around longitudinal axis A-A' of interventional device 31 are separated by gaps $G_1$, $G_2$, $G_n$.

FIG. 3 illustrates in plan-view a third embodiment of the invention in which ultrasound receivers $R_1$, $R_2$, $R_n$ of first sensor array 32 that are wrapped around longitudinal axis A-A' of interventional device 31 are separated by gaps $G_1$, $G_2$, $G_n$. Moreover, in the third embodiment the angle $\alpha_1$, $\alpha_2$, $\alpha_n$ subtended by each gap $G_1$, $G_2$, $G_n$ from the axis A-A' is less than or equal to the angle $\beta_1$, $\beta_2$, $\beta_n$ subtended by the width W of each ultrasound receiver from the axis A-A'. As illustrated with reference to FIG. 1C, the sensitivity of the interventional device to an ultrasound beam is reduced in the gaps between each ultrasound sensor. Advantageously the arrangement of the third embodiment reduces the total rotational angle over which the interventional device has low-sensitivity to ultrasound, thereby improving the accuracy with which the angular rotation can be determined.

Figure 4:
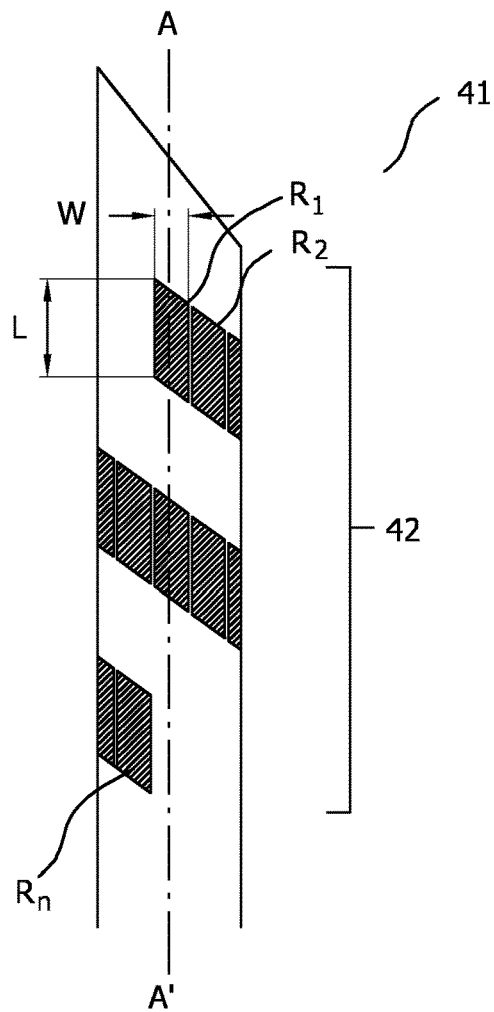
FIG. 4 illustrates in side-view a fourth embodiment of the invention in which first linear sensor array 42 that includes ultrasound receivers $R_{1 \ldots n}$ is attached to a substrate and the substrate is wrapped around longitudinal axis A-A' of interventional device 41 in the form of a spiral.

FIG. 4 illustrates in side-view a fourth embodiment of the invention in which first linear sensor array 42 that includes ultrasound receivers $R_{1...n}$ is attached to a substrate and the substrate is wrapped around longitudinal axis A-A' of interventional device 41 in the form of a spiral. The substrate may for example be a foil that is formed from a polymer such as PET, PMMA, PVDF and the like. The substrate may include electrical wires or tracks that are electrically connected to the receivers for making electrical contact to an external electrical circuit. As described above, a drawback to improving the rotational sensitivity of the interventional device by reducing the width W of each ultrasound receiver is the reduction in signal detected by each receiver. The arrangement in FIG. 4 compensates for the reduced width of each receiver by providing a plurality of individual receivers that each view the same, or an overlapping angular range. Moreover the individual receivers can be grouped together dynamically, for example using external electrical circuitry. This can be used to provide an increased signal across any predetermined rotational range. For example, interventional device 41 could be configured to operate in a first mode in which the signals from a first receiver group in which each receiver is sensitive to a portion of a first angular range are grouped together electronically and summed to provide a first rotation signal having a first angular-resolution, or in a second mode in which the signals from a second receiver group in which each receiver is sensitive to a portion of a second angular range are grouped together electronically and summed to provide a second rotation signal having a second angular-resolution. Thus, relatively higher or relatively lower angular resolution may be achieved by dynamically adjusting the receiver grouping. The spiral wrapping arrangement of FIG. 4 provides a robust method of attaching the ultrasound transducers $R_{1...n}$ and the electrical interconnections associated therewith to interventional device 41. Moreover it provides an efficient arrangement for routing the electrical interconnections to the proximal end of the interventional device where it may for example interface with a signal analysis unit and/or a processor.

Figure 5:
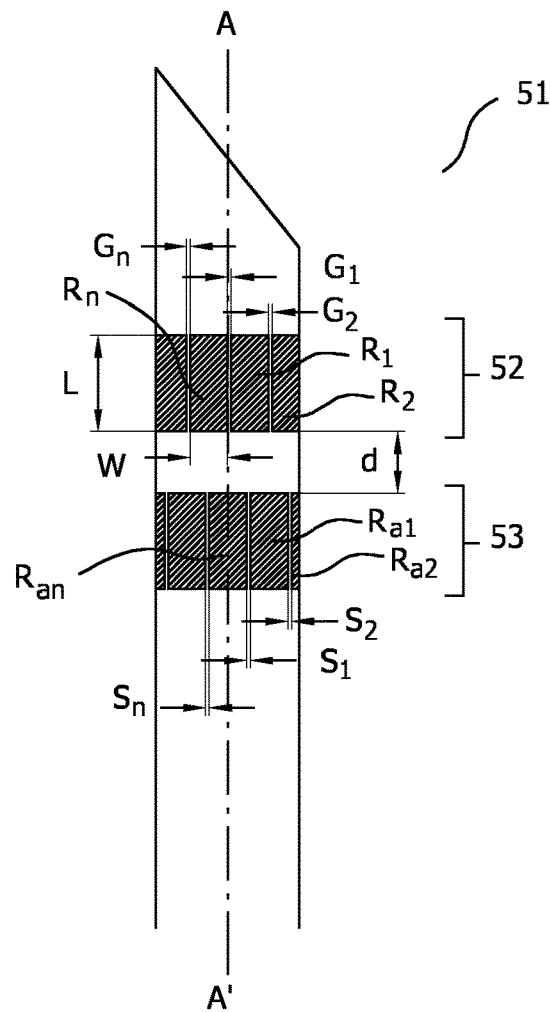
FIG. 5 illustrates in side-view a fifth embodiment of the invention in which first linear sensor array 52 and second linear sensor array 53 are both wrapped around longitudinal axis A-A' of interventional device 51.

FIG. 5 illustrates in side-view a fifth embodiment of the invention in which first linear sensor array 52 and second linear sensor array 53 are both wrapped around longitudinal axis A-A' of interventional device 51. Second linear sensor array 53 includes a plurality of ultrasound receivers $R_{a1}$, $R_{a2}$, $R_{an}$, each separated by a space $S_1$, $S_2$, $S_n$. Second linear sensor array 53 is wrapped around interventional device 51 circumferentially with respect to its axis A-A' such that each gap $G_1$, $G_2$, $G_n$, between the ultrasound receivers of the first linear sensor array 52 coincides with a receiver of the second linear sensor array $R_{a1}$, $R_{a2}$, $R_{an}$, in a lengthwise direction with respect to the axis A-A'. With reference to FIG. 1C, a relatively smaller ultrasound receiver signal is detected at rotational angles Θ that coincide with a gap between the ultrasound receivers in an array, as compared to at rotational angles that coincide with an ultrasound receiver. Thus the arrangement 51 of FIG. 5 in which ultrasound receivers of the second linear sensor array 53 coincide with the gaps of the first linear sensor array in a lengthwise direction with respect to the axis A-A', provides improved rotational sensitivity at rotational angles that correspond to the gaps of the first linear sensor array 52.

Preferably in the fifth embodiment the first linear sensor array 52 and the second linear sensor array 53 are axially separated with respect to the axis A-A' by a distance, d, that is greater than or equal to 1 mm. An ultrasound receiver position from the first linear sensing array 52 that is closest to the ultrasound beam source provides a point on the interventional device that is indicative of its position and its rotation. Likewise an ultrasound receiver position from the second linear sensing array 53 that is closest to the ultrasound beam source provides a second point on the interventional device that is indicative of its position and its rotation. Because the positions of these nearest-receivers are fixed with respect to the interventional device, together these points can be used to determine a trajectory of the interventional device. Improved sensitivity to the trajectory is provided by offsetting the two linear sensor arrays along the axis of the interventional device by at least 1 mm.

Figure 6:
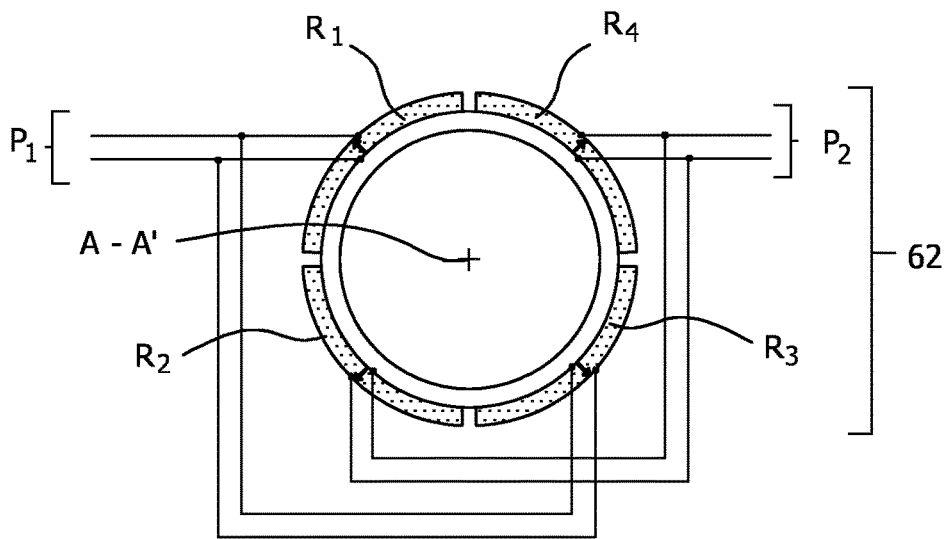
FIG. 6 illustrates in plan-view a sixth embodiment of the invention in which first linear sensor array 62 comprising an even number of ultrasound receivers $R_1$, $R_2$, $R_3$, $R_4$ are wrapped around longitudinal axis A-A' of interventional device 61 and in which the ultrasound receivers are arranged in diametrically-opposing pairs $P_1$, $P_2$, with respect to the axis.

FIG. 6 illustrates in plan-view a sixth embodiment of the invention in which first linear sensor array 62 comprising an even number of ultrasound receivers $R_1$, $R_2$, $R_3$, $R_4$ are wrapped around longitudinal axis A-A' of interventional device 61 and in which the ultrasound receivers are arranged in diametrically-opposing pairs $P_1$, $P_2$, with respect to the axis. Moreover in the sixth embodiment, each ultrasound receiver comprises a piezoelectric element having a polling vector, as indicated by the arrows in each of $R_1$, $R_2$, $R_3$, $R_4$. Furthermore, as illustrated in FIG. 6, the ultrasound receivers in each pair are arranged such that for each pair both: i) the polling vectors of the ultrasound receivers are mutually opposed with respect to the axis A-A'; and ii) the ultrasound receivers are electrically connected in parallel such that their polling vectors are mutually opposed.

Piezoelectric elements inherently have such a polling vector, this being indicative of the polarity of the electrical signal that will be generated across the electrodes of the piezoelectric element when the compressive phase of ultrasound wave impinges thereupon. Thus the arrangement of FIG. 6 provides that the combined signal from each receiver pair is indicative of the difference in their detected signals. In so doing, the combined signal from the closest detector in the pair to the ultrasound beam is enhanced, thereby improving the signal to noise ratio of the detected signals from each pair. Moreover, by providing the signals in pairs, the number of electrical connections that needs to be made to the distal end of the interventional device in order to analyze and/or process the detected signals, is reduced, thereby simplifying the complexity of the electrical interconnections associated with the ultrasound receivers.

The ultrasound receivers in the described embodiments are preferably piezoelectric devices. Many types of hard or soft piezoelectric materials are suitable for use as such, these being well known in the art. However, preferably the ultrasound receivers are formed from a piezoelectric polymer. Piezoelectric polymers advantageously provide increased flexibility and thus may be conformally wrapped around the axis of an interventional device such as a needle. Suitable piezoelectric polymers include Polyvinylidene fluoride, i.e. PVDF, or a PVDF co-polymer such as polyvinylidene fluoride trifluoroethylene (P(VDF-TrFE)) or a PVDF terpolymer such as P(VDF-TrFE-CTFE). The ultrasound receiver may for example be formed by sandwiching the piezoelectric material and the electrical interconnections associated therewith between two pressure sensitive adhesive, i.e. PSA, surfaces of two PET sheets to form a foil in order to facilitate its attachment to the interventional device. The ultrasound transducers may in general be attached to the interventional device using a variety of techniques in addition to the use of a PSA layer from one of the above-described PET sheets. Such techniques include deposition, printing, and the use of adhesives.

Figure 7:
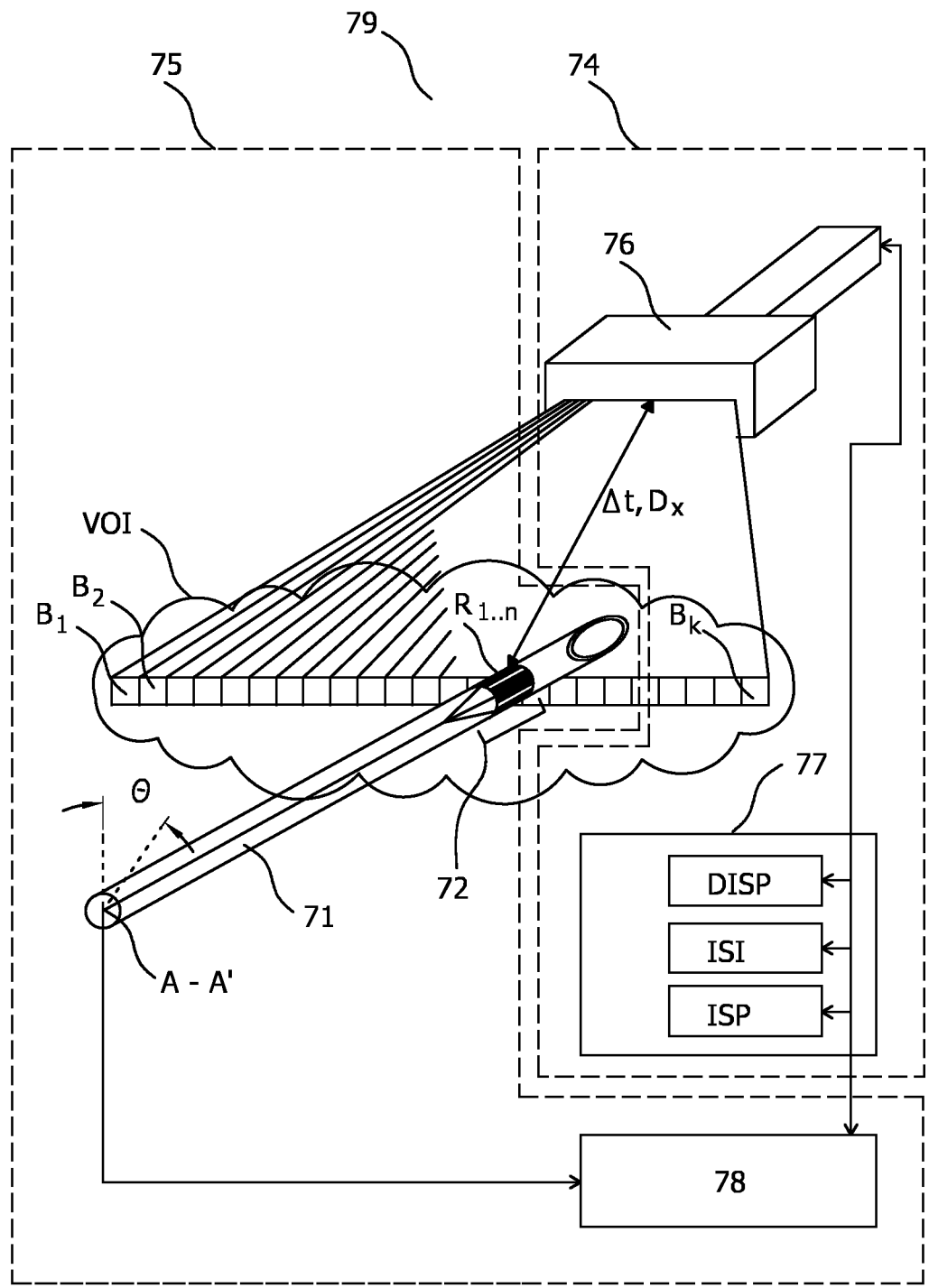
FIG. 7 illustrates an ultrasound imaging arrangement 79 in which various embodiments of the invention may be used, the arrangement including a beamforming ultrasound imaging system 74, and an ultrasound tracking unit 75.

FIG. 7 illustrates an ultrasound imaging arrangement 79 in which various embodiments of the invention may be used, the arrangement including a beamforming ultrasound imaging system 74, and an ultrasound tracking unit 75. Beamforming ultrasound imaging system 74 includes an exemplary 2D planar ultrasound imaging probe 76, and a console 77. As illustrated, 2D planar ultrasound imaging probe 76 generates an ultrasound field in the form of a fan comprising multiple ultrasound beams $B_{1...k}$. 2D planar ultrasound imaging probe 76 is operationally connected to console 77, for example by wired or wireless means, as indicated by the connecting arrow. Console 77 includes imaging system processor ISP, imaging system interface ISI and display DISP as shown. Console 77 may be used to supervise a medical procedure. 2D ultrasound imaging probe 76 includes a one-dimensional array of ultrasound transceivers (not shown) for transmitting and receiving ultrasound energy from a volume of interest VOI. Console 77 may also include electronic driver and receiver circuitry (not shown) that is configured to amplify and/or to adjust the phase of signals transmitted by or received by 2D ultrasound imaging probe 76 in order to generate and detect ultrasound signals in beams $B_{1...k}$.

The electronic driver and receiver circuitry may thus be used to steer the emitted and/or received ultrasound beam direction. Console 77 may also include a memory (not shown) for storing programs and applications. The memory may for example store ultrasound beam control software that is configured to control the sequence of ultrasound signals transmitted by and/or received by 2D ultrasound imaging probe 76. It is to be noted however that whilst some of the ultrasound imaging system items are described above as being located within console 77, some of these items may alternatively be located within 2D ultrasound imaging probe 76, as is the case for example in the Philips VISIQ ultrasound imaging system.

Ultrasound tracking unit 75 includes a tracking processor 78 and interventional device 71, the two units being in communication by means of either wired or wireless communication as indicated by the connecting arrow. Wireless communication may for example be provided using an optical, infrared, or an RF communication link. Ultrasound tracking unit 75 may also include electronic circuitry (not shown) that is configured to amplify signals detected by ultrasound receivers $R_1$, $R_2$, $R_n$, that are disposed circumferentially about longitudinal axis A-A' of interventional device 71.

In operation, ultrasound tracking unit 75 may be used to track the rotation, and furthermore the position and orientation, of interventional device 71 in one of the ultrasound beams $B_{1 \ldots k}$ of 2D ultrasound imaging probe 76.

In order to track the rotation of interventional device 71 in one of the ultrasound beams $B_{1 \ldots k}$ of 2D ultrasound imaging probe 76, the following method steps can be used:

receiving from each ultrasound receiver $R_1$, $R_2$, $R_n$ of the first linear sensor array 72, signals indicative of transmitted ultrasound pulses of the beamforming ultrasound imaging system. Here transmitted pulses refers to pulses that have been transmitted from the beamforming ultrasound system, i.e. the 2D ultrasound imaging probe 76;

comparing the received signals. Here the comparison may include comparing the magnitudes or the amplitudes or the times of the detected signals;

associating the ultrasound receiver $R_1$, $R_2$, $R_n$ having either the maximum received signal, or the earliest received signal, with the origin of the ultrasound beam. Here the association step identifies the rotational position Θ of the receiver that is rotationally closest to the origin, i.e. the zenith, of the ultrasound beam, i.e. one of beams $B_{1 \ldots k}$.

In order to determine a distance of interventional device 71 from the source of one of the ultrasound beams $B_{1 \ldots k}$ of 2D ultrasound imaging probe 76, the following method steps can be used:

compute the time delay Δt between transmission of the ultrasound beam and its detection by the ultrasound receiver;

determine the distance $D_X$ between the source of the ultrasound beam and the ultrasound receiver by multiplying the time delay by the speed of ultrasound propagation.

Specifically the distance determined above is the distance between the ultrasound beam's origin and the portion of interventional device 71 to which the nearest ultrasound receiver of the first linear sensor array 72 is attached, that is determined using the so-described time-of-flight method. Note that although the speed of ultrasound propagation may vary within the volume of interest VOI, this does not translate into a distance, or range error in the corresponding ultrasound image because such variation is also reflected on the ultrasound images.

In order to identify in which ultrasound beam from a plurality of ultrasound beams $B_{1 \ldots k}$ emitted by the beamforming ultrasound imaging system 74 the ultrasound receiver $R_1$, $R_2$, $R_n$ associated with the maximum signal is located, the following method step can be used:

correlating the emitted beam sequence of the plurality of beams with the signals received by the ultrasound receiver $R_1$, $R_2$, $R_n$ having the maximum received signal.

In other words, the time of emission of each beam of the plurality of beams is matched with the time of detection of the maximum signal, whilst compensating for the time delay between transmission and detection, to identify the beam $B_{1 \ldots k}$ associated with the maximum signal. In so doing the angle of the ultrasound receiver in relation to the beamforming imaging system is provided because this angle is defined by the beam angle of the identified beam.

The identification of which ultrasound beam the detector is located in is based on the following principle. A 2D ultrasound imaging probe emits ultrasound beams that regularly sample the volume of interest VOI in an array of beams $B_{1 \ldots k}$. The temporal signals detected by the ultrasound receivers $R_1$, $R_2$, $R_n$ during the acquisition of one image by the ultrasound imaging system are formatted in a two-dimensional $B_{1 \ldots k}$ by time "data matrix". In order to determine which beam the ultrasound receiver is in, the time of detection is correlated, i.e. compared with the time of emission of each beam to determine the position that best fits the detected signals. In order to receive angular position information with a better resolution than that given by the spacing of the ultrasound beams, a maximum intensity projection "MIP" of the "data matrix" over the time dimension is performed to yield a 1D MIP vector on which a Gaussian fit is applied. The Gaussian center is used to estimate the angular coordinates of the receiver in the ultrasound coordinate system.

Together, the methods described above, i.e. the tracking of the rotation, the determining of the distance, and the identification of the ultrasound beam, provide an accurate indication of the position and rotation of the interventional device respective the beamforming ultrasound imaging system. With reference to FIG. 7, these may subsequently be used to register an ultrasound image provided by the beamforming ultrasound imaging system 74, with a second image that includes the interventional device 71 and which is provided by a second imaging system (not shown in FIG. 7). The registration may be performed by aligning the coordinate systems of the ultrasound and the second imaging system based on the position and/or the orientation of the interventional device as provided by ultrasound tracking unit 75. The second imaging system may for example be a PET, a SPECT, a CT, an x-ray or an MR imaging system. The ultrasound image provides, in the above described case, a 2D image slice through a volume of interest. By combining this image with that of the second imaging system, improved navigation is provided because features that are visible in the second image often provide valuable landmarks. The image from the second imaging system may be a live image, or a previously-generated "navigation" image.

Any of the above-described methods may for example be carried out by tracking processor 78 or by imaging system processor ISP of console 77 illustrated in FIG. 7. Moreover the functions of each of these units may be combined into a single processor or distributed amongst separate processors. Moreover the method may be recorded in the form of instructions which when executed on a processor cause the processor to carry out these method steps. The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk—read only memory "CD-ROM", compact disk—read/write "CD-R/W", Blu-Ray™ and DVD.

It shall be understood that the device of claim 1, the method of claim 9 and the computer program product of claim 13 have similar and/or identical preferred embodiments, in particular, as defined in the dependent claims. Moreover the embodiments, whilst described individually, can also be combined, as defined in the dependent claims.

The invention claimed is:

1. An ultrasound tracking device comprising:
 an interventional device, the interventional device comprising:
  an elongated body having a longitudinal axis; and
  a first linear sensor array comprising a plurality of ultrasound receivers, wherein each ultrasound receiver has a length and a width, wherein the sensor array extends along the width direction, wherein each ultrasound receiver is configured to receive ultrasound signals from an external beamforming ultrasound imaging system, and
  wherein the first linear sensor array is wrapped circumferentially around the elongated body with respect to the longitudinal axis such that the length of each ultrasound receiver is arranged lengthwise with respect to the longitudinal axis; and
 a processor configured to determine a rotation of the interventional device relative to the longitudinal axis of the elongated body based on correlation of the received ultrasound signals with ultrasound signals transmitted by the external beamforming ultrasound imaging system.

2. The ultrasound tracking device according to claim 1 wherein a length of at least one ultrasound receiver of the plurality of ultrasound receivers is greater than a width of the at least one ultrasound receiver.

3. The ultrasound tracking device according to claim 1 wherein the ultrasound receivers are each separated by a gap, and wherein an angle subtended by each gap from the longitudinal axis is less than or equal to an angle subtended by the width of each ultrasound receiver from the longitudinal axis.

4. The ultrasound tracking device according to claim 3 further comprising a second linear sensor array, wherein the second linear sensor array comprises a plurality of ultrasound receivers each separated by a space, and wherein the second linear sensor array is wrapped around the elongated body circumferentially with respect to the longitudinal axis such that each gap of the first linear sensor array coincides with a receiver of the second linear sensor array in a lengthwise direction with respect to the longitudinal axis.

5. The ultrasound tracking device according to claim 4 wherein the first linear sensor array and the second linear sensor array are axially separated with respect to the longitudinal axis by a distance that is greater than or equal to 1 mm.

6. The ultrasound tracking according to claim 1 wherein the first linear sensor array is attached to a substrate and the substrate is wrapped around the interventional device in a form of a spiral.

7. The ultrasound tracking device according to claim 1 wherein the first linear sensor array comprises an even number of ultrasound receivers that are arranged in diametrically-opposing pairs with respect to the longitudinal axis, wherein each ultrasound receiver comprises a piezoelectric element having a polling vector, and
 wherein the ultrasound receivers in each pair are arranged such that for each pair both:
  the polling vectors of the ultrasound receivers are mutually opposed with respect to the longitudinal axis; and
  the ultrasound receivers are electrically connected in parallel such that the polling vectors are mutually opposed.

8. The ultrasound tracking device according to claim 7 wherein the ultrasound receivers are formed from a piezoelectric polymer.

9. The ultrasound tracking device of claim 1, wherein the rotation is determined by comparing relative magnitudes of the ultrasound signals received by each of the plurality of the ultrasound receivers.

10. The ultrasound tracking device of claim 1, wherein each ultrasound receiver is configured to receive ultrasound signals from the external beamforming ultrasound imaging system to enable determination of a position and orientation of the interventional device.

11. A method comprising:
 receiving, from each of a plurality of ultrasound receivers of a first linear sensor array, signals indicative of transmitted ultrasound pulses of an external beamforming ultrasound imaging system, wherein the plurality of ultrasound receivers are wrapped circumferentially around an elongated body of an interventional device with respect to a longitudinal axis of the elongated body such that a length of each ultrasound receiver is arranged lengthwise with respect to the longitudinal axis;
 comparing the received signals;
 associating an ultrasound receiver having either a maximum received signal, or an earliest received signal, with an origin of an ultrasound beam; and
 determining a rotation of the interventional device relative to the longitudinal axis of the elongated body based on the association of the ultrasound receiver with the origin of the ultrasound beam.

12. The method of claim 11 further comprising:
 determining a distance of the ultrasound receiver associated with the maximum received signal from the origin of the ultrasound beam based on a time delay between transmission of the ultrasound beam and detection of the ultrasound beam by the ultrasound receiver.

13. The method of claim 12 further comprising:
 identifying in which ultrasound beam from a plurality of ultrasound beams emitted by the beamforming ultrasound imaging system the ultrasound receiver associated with the maximum received signal is located by correlating the identified ultrasound beam of the plurality of beams with the signals received by the ultrasound receiver having the maximum received signal.

14. The method of claim 13 further comprising using a position and rotation of the interventional device relative to the beamforming ultrasound imaging system to register an ultrasound image provided by the beamforming ultrasound imaging system with a second image that includes the interventional device and which is provided by a second imaging system; the position being determined based on the determined distance and the identified ultrasound beam; and the rotation being determined based on the ultrasound receiver associated with the maximum received signal.

15. The method of claim 11, wherein the rotation is determined by comparing relative magnitudes of the signals received by each of the plurality of the ultrasound receivers.

16. The method of claim 11, further comprising determining a position and orientation of the interventional device based on the received signals.

17. A non-transitory computer readable medium having stored thereon instructions, which when executed by processing circuitry, are configured to cause the processing circuitry to receive, from each of a plurality of ultrasound receivers of a first linear sensor array, signals indicative of transmitted ultrasound pulses of an external beamforming ultrasound imaging system, wherein the plurality of ultrasound receivers are wrapped circumferentially around an elongated body of an interventional device with respect to a longitudinal axis of the elongated body such that a length of each ultrasound receiver is arranged lengthwise with respect to the longitudinal axis;
 comparing the received signals;
 associating an ultrasound receiver having either a maximum received signal, or an earliest received signal, with an origin of an ultrasound beam; and
 determining a rotation of the interventional device relative to the longitudinal axis of the elongated body based on the association of the ultrasound receiver with the origin of the ultrasound beam.

18. The non-transitory computer readable medium of claim 17, wherein the rotation is determined by comparing relative magnitudes of the signals received by each of the plurality of the ultrasound receivers.

19. The non-transitory computer readable medium of claim 17, further comprising code that, when executed by the processing circuitry, is configured to cause the processing circuitry to determine a position and orientation of the interventional device based on the received signals.

* * * * *